(12) United States Patent
Masaki et al.

(10) Patent No.: US 6,999,172 B2
(45) Date of Patent: Feb. 14, 2006

(54) OPTICAL APPARATUS

(75) Inventors: Fumitaro Masaki, Tochigi (JP); Akira Miyake, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 310 days.

(21) Appl. No.: 10/280,806

(22) Filed: Oct. 25, 2002

(65) Prior Publication Data

US 2003/0081210 A1    May 1, 2003

(30) Foreign Application Priority Data

Oct. 26, 2001    (JP)    ............................. 2001-328660

(51) Int. Cl.
  *G01J 4/00*    (2006.01)
  *G02F 1/07*    (2006.01)
  *G02B 5/30*    (2006.01)

(52) U.S. Cl. ...................... 356/364; 356/367; 356/368; 250/225; 359/245; 359/483

(58) Field of Classification Search ........ 356/364–370, 356/445; 250/225, 208.1, 201.3, 201.5; 359/245–246, 359/483, 487, 833–834, 488, 559, 613–614, 359/240

See application file for complete search history.

(56) References Cited

U.S. PATENT DOCUMENTS

| | | | | |
|---|---|---|---|---|
| 3,968,376 A | * | 7/1976 | Pierce et al. ............. | 250/493.1 |
| 5,075,893 A | * | 12/1991 | Epstein et al. ............... | 372/108 |
| 5,239,365 A | * | 8/1993 | Inoue ......................... | 356/367 |
| 5,617,076 A | * | 4/1997 | Stern .......................... | 340/583 |
| 5,627,645 A | * | 5/1997 | Imagawa et al. ........... | 356/364 |
| 5,764,363 A | * | 6/1998 | Ooki et al. ................ | 356/364 |
| 5,929,995 A | * | 7/1999 | Johs ........................... | 356/369 |
| 6,046,811 A | * | 4/2000 | Wolff et al. ................. | 356/369 |
| 6,084,675 A | * | 7/2000 | Herzinger et al. .......... | 356/369 |
| 6,137,618 A | * | 10/2000 | Herzinger .................. | 359/245 |
| 6,141,102 A | * | 10/2000 | Johs et al. .................. | 356/364 |
| 6,356,578 B1 | * | 3/2002 | Yin ............................ | 372/107 |
| 6,411,370 B1 | * | 6/2002 | Rajchel et al. ................ | 356/3 |
| 6,768,422 B1 | * | 7/2004 | Schofield et al. ........... | 340/602 |
| 6,795,184 B1 | * | 9/2004 | Herzinger et al. .......... | 356/369 |

FOREIGN PATENT DOCUMENTS

| | | |
|---|---|---|
| JP | 07-094396 | 4/1995 |
| JP | 2001-264696 | 9/2001 |

OTHER PUBLICATIONS

K. Jacobi et al., "Small rotating triple-reflection polariser for a uv discharge lamp", Journal of Physics E: Scientific Instruments, vol. 11, No. 10, Oct. 1978, UK, pp. 982-983.

M. Suzuki et al., "Direct measurement of magnetic circular dichroism and Kerr rotation spectra in vacuum ultraviolet using four-mirror polarizer", Review of Scientific Instruments, American Institute of Physics, New York, US, vol. 66, No. 2, Part 2, Feb. 1, 1995, pp. 1589-1591.

(Continued)

*Primary Examiner*—Gregory J. Toatley, Jr.
*Assistant Examiner*—Sang H. Nguyen
(74) *Attorney, Agent, or Firm*—Morgan & Finnegan, LLP

(57) ABSTRACT

An optical apparatus that measures a polarization dependent characteristic of a measured object includes a light source for emitting non-linearly polarized light in an extreme ultraviolet region or an X-ray region, and a rotary polarizer for reflecting the light emitted from the light source, the polarizer including a set of mirrors repeating three or more reflections and being arranged such that an optical axis of incident light and that of outgoing light are aligned with the same straight line.

16 Claims, 13 Drawing Sheets

OTHER PUBLICATIONS

R. L. Johnson, et al., "Spectroscopic ellipsometry with synchrotron radiation", Review of Scientific Instruments, American Institute of Physics, New York, US, vol. 60, No. 7, Part 2B, Jul. 1, 1989, pp. 2209-2212.

T. Koide et al., "Polarization characterization of circularly polarized vacuum-ultraviolet and soft-x-ray helical undulator radiation", Review of Scientific Instruments, American Institute of Physics, New York, US, vol. 66, No. 2, Part 2, Feb. 1, 1995, pp. 1923-1925.

A copy of an European Search Report mailed Jan. 30, 2004, issued in a counterpart foreign application.

Kondo et al., "Development of an EUV Reflectometer using a laser-plasma X-ray source", Proceedings, SPIE, vol. 4144, 2000, pp. 76-81.

Yamamoto et al., "Soft-x-ray polarization measurement with a laboratory reflectometer", Proceedings, SPIE, vol. 1720, 1992, pp. 190-194.

Höchst et al., "Performance evaluation of a soft x-ray quadruple reflection circular polarizer", Rev. Sci. Instrum., 66 (2), Feb. 1995, pp. 1598-1600.

Koide et al., "Polarization characterization of circularly polarized vacuum-ultraviolet and soft-x-ray helical undulator radiation", Rev. Sci. Instrum., 66 (2), Feb. 1995, pp. 1923-1925.

* cited by examiner

OPTICAL AXIAL DIRECTION

US 6,999,172 B2

OPTICAL APPARATUS

BACKGROUND OF THE INVENTION

The present invention relates generally to measuring apparatuses, and more particularly to a measuring apparatus that uses as the light source a light emitting source in an extreme ultraviolet ("EUV") region or an X-ray region.

The recent developments of X-ray, soft X-ray, and EUV optics have expanded their applications in a variety of field. In particular, a field of evaluation of optical elements and the like for the EUV light has attracted attention. The polarization of light needs to be considered in evaluating the reflectance of an optical element through irradiation, because the property that an optical element indicates generally differs from the polarization of light. As shown in FIG. 18, polarized light with an electric field vector perpendicular to the paper, and against a specular surface 1000a is defined as s-polarized light, and polarized light with an electric field vector perpendicular to the s-polarized light and vertical to a wave number vector is defined as p-polarized light. Where $I_s$ is intensity of the s-polarized light and $I_p$ is intensity of the p-polarized light, the degree of polarization P is given in the following equation:

$$P=(I_s-I_p)/(I_s+I_p) \tag{1}$$

Here, FIG. 18 is a schematic view showing how the light is polarized.

For example, there is a multilayer mirror having high reflectance in the X-ray or soft X-ray regions, but the reflectance of such a multilayer reflecting mirror differs with polarization of incident light. FIG. 19 shows reflectance characteristics obtained by calculation about a multilayer mirror as a five layer pairs pair with a thickness of 9.6 nm combining the molybdenum (Mo) and silicon (Si) layers when the incident angle of light is set to 42.6°. This figure adopts the horizontal axis as wavelengths of light incident on the multilayer mirror, and the longitudinal axis as reflectance of the multilayer mirror. In other words, as to light that mixes p-polarized light and s-polarized light in it, the values differ depending on the degree of polarization, and therefore it is difficult to measure reflectance with accuracy. Thus, to accurately measure reflectance, it is necessary to separate linearly polarized light as the p-polarized light or as the s-polarized light.

Conventionally, however, it has not been easy to create linearly polarized light from a light source of non-polarized light for use in measurement, and thus the linearly polarized light with a high degree of polarization and planes of polarization that can be switched.

For example, as an apparatus that accurately measures reflectance, a reflectometer has been used conventionally that uses a synchrotron light source. FIG. 20 is a schematic view of a reflectometer 2000 that uses a synchrotron light source. The reflectometer 2000 uses synchrotron radiation from a bending magnet of a light source 2100. Synchrotron radiation from the bending magnet has linearly polarized light with an electric field vector in a plane of an electron orbit. Therefore, via a subsequent optical system 2200, light separated as the p-polarized light or the s-polarized light is irradiated onto a measured object 2300, and thus it is possible to measure reflectance using a detector 2400 in consideration of polarized light. However, since the reflectometer 2000 using a synchrotron light source has synchrotron radiation from the light source 2100 that is always linearly polarized into the plane of the electron orbit, there is no other choice than changing the direction of the measured object 2300 so as to shift the direction of polarization onto the measured object 2300 (i.e., choose between s-polarized light and p-polarized light). Accordingly, in order to change the direction of the measured object 2300, it has been necessary to turn the chamber containing the measured object 2300, which usually weighs several hundred kilograms, thus making it very difficult to choose between s-polarized light and p-polarized light. Furthermore, a synchrotron light source itself has been of a very large scale, and highly expensive.

Thus, a reflectometer using a laser producing plasma light source (hereinafter called an LPP light source), which is small-sized and low-priced compared to the synchrotron light source, is proposed in the Proceedings SPIE Vol. 4144 (2000), pp. 76–81, "Development of an EUV Reflectometer using a laser-plasma X-ray source." Such an apparatus determines multilayer parameters by curve-fitting data obtained in measurement. As the polarization of light from a light source is assumed to be random, and s-polarized light is estimated to be 5% from the calculation of an optical system arrangement, there still remains uncertainty in the degree of polarization, and errors are produced in reflectance, thus being unable to determine highly precise multilayer film parameters.

Further, a reflectometer, which circumvents the above problems by inserting a transmission-type multilayer polarizer having excellent polarization characteristics, has been proposed in the Proceedings of SPIE Vol. 1720 (1992) pp. 190–194, "Soft-x-ray polarization measurement with a laboratory reflectometer." Such an apparatus, though it employs an LPP light source, makes it possible to measure reflectance, separating polarized light by attaching a transmission-type multilayer polarizer with molybdenum (Mo) and silicon (Si) laminated. However, considering transmittance, it is necessary to contain the thickness of the multilayer polarizer (the thickness including a multilayer film and a plate) within several hundred nm or less, and accordingly, it is difficult to manufacture and easy to break, and has heat-resisting problems. In addition, when a non-polarized soft X-ray with a wavelength of 12.8 nm transmits a polarizer with molybdenum (Mo) and silicon (Si) laminated in 41 layers, a transmittance intensity ratio of s-polarized light and p-polarized light is only as much as 0.2, thus being unable to obtain a high degree of polarization.

In order to obtain a desired polarization state, use of a reflection polarizer that is easy to manufacture and excellent in durability is proposed in Rev. Sci. Instrum. 66 (2) pp. 1598–1600, February 1995, "Performance evaluation of a soft x-ray quadruple reflection circular polarizer." However, this merely turns linearly polarized light into circularly polarized light using a structure of four multilayer mirrors, and thus, it cannot be used for polarization dependent characterization of a highly precise sample.

Use of two polarizers structured in three multilayer mirrors that rotate around the optical axis is proposed in the Rev. Sci. Instrum. 66 (2) pp. 1923–1925, February 1995, "Polarization characterization of circularly polarized vacuum-ultraviolet and soft-x-ray helical undulator radiation." However, this is an apparatus that measures characteristics of a synchrotron light source and degrees of circularly polarized light, thus being used for different purposes.

For the above apparatuses, use of a large-scale structure is unavoidable to perform highly accurate measurement in consideration of polarization and by using synchrotron. A structure suitable for highly accurate measurement by using an LPP light source has not been realized that is a small-sized and low-priced light source using non-linearly polarized light.

BRIEF SUMMARY OF THE INVENTION

Accordingly, the present invention has an exemplified object to provide an optical apparatus that can easily change polarization planes with a high degree of polarization, and can easily perform highly accurate measurement, even if a non-linearly polarized light source is used.

An optical apparatus of one aspect of the present invention that measures a polarization dependent characteristic of a measured object includes a light source for emitting non-linearly polarized light in an extreme ultraviolet region or an X-ray region, and a rotary polarizer for reflecting the light emitted from the light source, the polarizer including a set of mirrors repeating three or more reflections and being arranged such that an optical axis of incident light and that of outgoing light are aligned with the same straight line. A polarization plane of the light used to irradiate the measured object may vary when the rotary polarizer rotates. This optical apparatus uses the polarizer that does not change the optical axis of the incident light and that of the outgoing light, can change a non-linearly polarized light into linearly polarized light, irradiate it to a measured object, and measure the polarization dependent characteristic.

The polarizer may rotate around the optical axis of the incident light as a central axis. Hereby, planes of polarization relative to the measured object can be switched. In other words, a mere rotation of the polarizer may select the s-polarized light or the p-polarized light. The polarizer may be retractable against a light path of the light emitted from the light source. Thus, non-polarized light can be irradiated to the measured object. The optical apparatus further includes an optical system that condenses the light emitted from the light source, and an optical system that directs the outgoing light from the polarizer to the measured object, and the polarizer may be arranged in place substantially conjugate with the optical system. Thereby, influences of an angular shift and a positional shift due to a design error and/or installation error of the polarizer can be prevented.

The light source may be an LPP light source. The optical apparatus may further include a monochrometer for introducing to the polarizer light having a desired wavelength among the light from the light source. The set of mirrors may include a multilayer mirror having a predetermined layer thickness distribution, and moving in accordance with the wavelength of the light from the monochrometer. The polarization dependent characteristic of the measured object may be reflectance. The polarization dependent characteristic of the measured object may be a spectrum of a photoelectron emitted from the measured object. The polarizer may be arranged close to the measured object, whereby an influence of an angular shift due to a design error and/or installation error of the polarizer can be prevented.

An optical element as still another aspect of the present invention has polarization dependent characteristics that are measured by using the above optical apparatus, and the measured characteristics are more than specified values. Such an optical element may be a mirror, a diffraction grating, a light integrator, an optical film or a complex of these including, i.e., a mirror, a multi-mirrors a fly-eye mirrors, an aspheric mirrors, a diffraction grating, and a combination thereof.

An exposure apparatus as still another aspect of the present invention utilizes ultraviolet light, far ultraviolet light and vacuum ultraviolet light as exposure light, irradiates the exposure light to an object to be exposed via an optical system including the above optical elements, and exposes the object. Such an exposure apparatus exhibits operations similar to those of the above optical elements.

A device fabricating method as still another aspect of the present invention includes the steps of projecting and exposing the above object to be exposed using the above exposure apparatus, and performing a given process for the exposed object. Claims for the device fabricating method that exhibits operations similar to those of the above exposure apparatus cover devices as their intermediate products and finished products. Moreover, such devices include semiconductor chips such as LSIs and VLSIs, CCDs, LCDs, magnetic sensors, thin-film magnetic heads, etc.

Other objects and further features of the present invention will become readily apparent from the following description of the embodiments with reference to accompanying drawings.

DETAILED DESCRIPTION OF THE PREFERRED EMBODIMENTS

Figure 1:
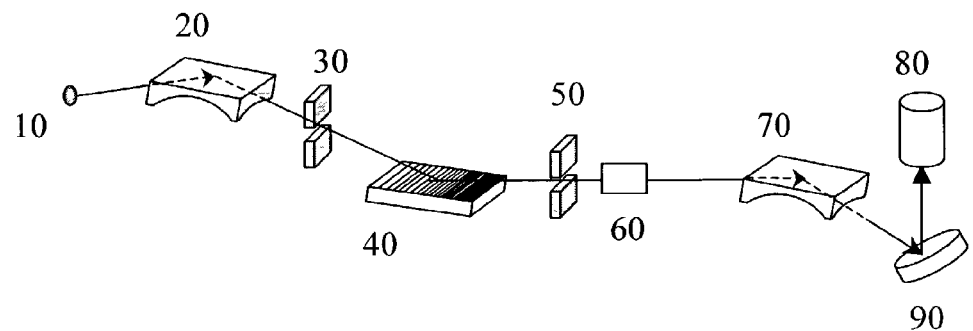
FIG. 1 is a schematic view of a reflectance measuring apparatus as an exemplified optical apparatus of the present invention.

Referring to the accompanying drawings, a description will now be given below of a reflectance measuring apparatus 1, and a photoelectron spectrometer 2, as examples of the optical apparatus of the present invention. Of course, the present invention is not limited to these embodiments, and within the sphere in which the object of this invention is achieved, each component may be alternatively substituted. Here, FIG. 1 is a schematic view of the reflectance measuring apparatus 1. As shown in FIG. 1, the reflectance measuring apparatus 1 includes a light source 10, a prefocusing mirror 20, a slit 30, a diffraction grating 40, a slit 50, a polarizer 60, a postfocusing mirror 70 and a detector 80, thus measuring reflectance of a measured object 90.

The light source 10 is a plasma light source (for example, LLP light source) in the EUV X-ray region, which emits a divergent pencil of rays that are isotropically non-polarized and have a continuous wavelength. The prefocusing mirror 20 takes in EUV light from the light source 10, and forms an image of the light source 10. By installing the slit 30 after the prefocusing mirror 20, limits are set to the size of the light source 10 taken in. The diffraction grating 40 diffracts incident light to different angles based on wavelengths, and thus, can split light by providing the slit 50 after it. A structure of the prefocusing mirror 20, the slit 30, the diffraction grating 40 and the slit 50 is called a Dragon-type monochrometer. Since a publicly known technique is applicable, a detailed description of it is omitted here. EUV light emitted from the light source 10 is almost non-polarized, monochromatic light right after the slit 50. The postfocusing mirror 70 takes in the EUV light from a slit 50, and forms an image on measured sample 90.

The polarizer 60 combines multiple multilayer mirrors, at least one of which is adapted such that it has an incident angle close to a Brewster angle, and by taking advantage of a difference in reflectance between s-polarized light and p-polarized light, non-polarized light is changed into linearly polarized light. A combination of multilayer mirrors is arranged such that the optical axis of the incoming light and that of the outgoing light of the polarizer 60 are on the same straight line (hereinafter, such a structure is called "a structure that does not change the optical axis").

Figure 2:
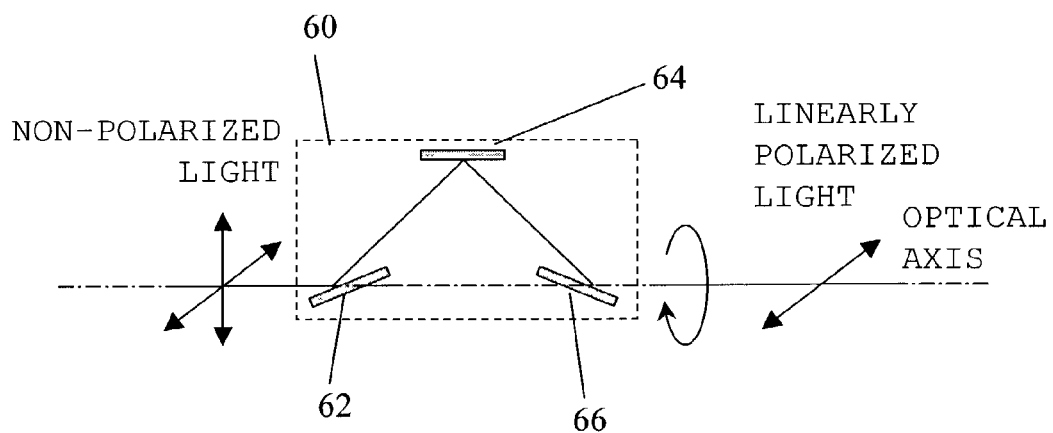
FIG. 2 is a schematic view of a polarizer shown in FIG. 1.
Figure 3:
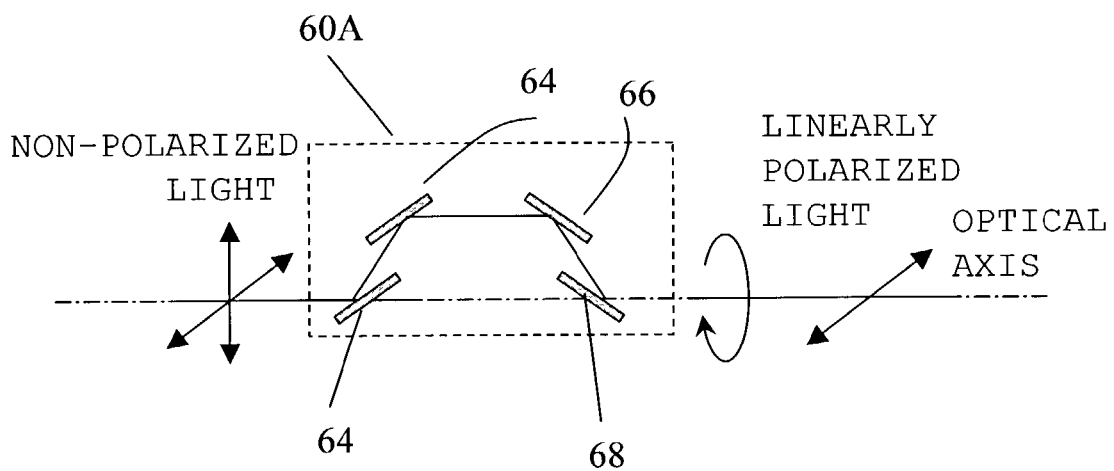
FIG. 3 is a schematic view of a variation of the polarizer shown in FIG. 2.

An example of a multilayer mirror arrangement of the polarizer 60 is shown in FIG. 2. FIG. 2 is a schematic view of the polarizer 60. As shown in FIG. 2, the polarizer 60 is structured such that the incident angle of a first multilayer mirror 62 is 66.3°, that of a second multilayer mirror 64 is 42.6°, and that of a third multilayer mirror 66 is 66.3°. Therefore, the polarizer 60 can realize a high degree of polarization since it does not change the optical axis, and the second multilayer mirror 64 is still close to the Brewster angle. The first to third multilayer mirrors 62~66 are Mo/Si multilayer mirrors, and as a matter of calculation, the ratio of p-polarized light to s-polarized light is $1 \times 10^{-3}$ when the wavelength is approximately 13.5 nm. The first and third multilayer mirrors 62 and 66 have a thickness of 20 nm and are a three layer pairs pair, and the second multilayer mirror 64 has a layer pairs thickness of 9.6 nm and is a five layer pairs pair. However, the multilayer mirrors making up the polarizer 60 are not limited to three mirrors. Any number of mirrors will do insofar as it is structured such that the optical axis of an incoming light and that of an outgoing light are not changed. For example, as shown in FIG. 3, it may be of a four-mirror structure by adding a fourth multilayer mirror 68. Here, FIG. 3 is a schematic view of a polarizer 60A that is a variation of the polarizer 60.

The polarizer 60 includes a drive mechanism (not shown), and it is possible to choose between s-polarized light and p-polarized light by turning the polarizer 60 around the optical axis as its rotation axis, thus switching the planes of polarization. Further, it is also possible to choose non-polarized light by using the drive mechanism (not shown) to move (put in and out) the polarizer 60 to a direction vertical to the optical axis. Use of non-polarized light and the polarizer 60 will make it possible to choose a direction of polarization only by a simple rotational operation.

Figure 4:
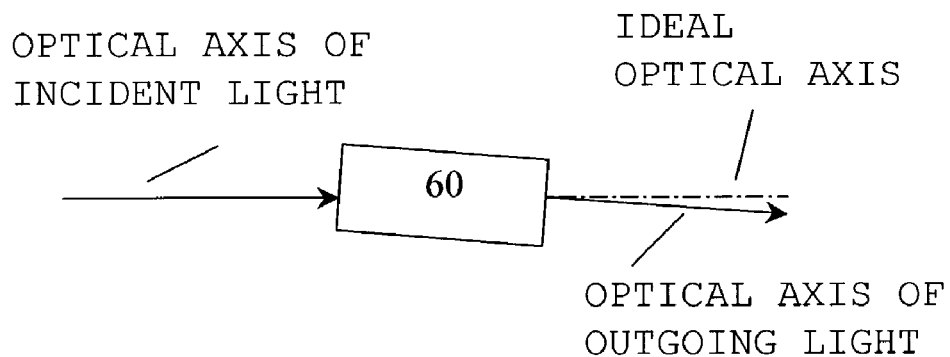
FIG. 4 is a view showing an angular shift of the optical axis of an outgoing light in the polarizer shown in FIG. 1.
Figure 5:
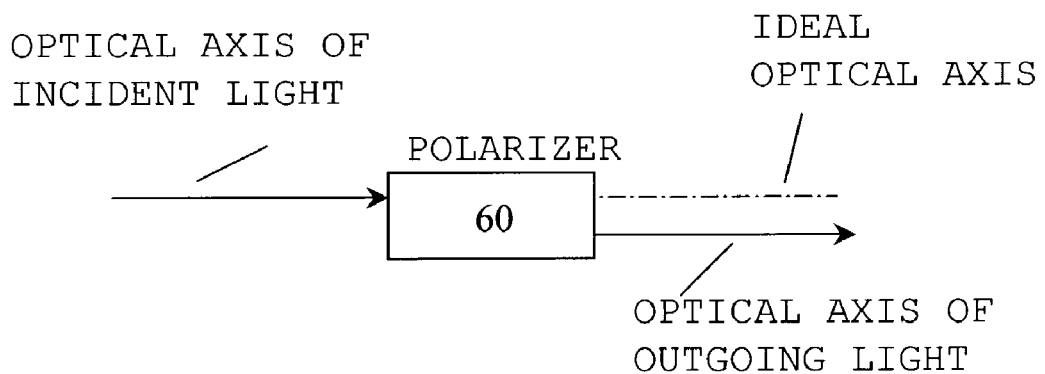
FIG. 5 is a view showing a positional shift of the optical axis of the outgoing light in the polarizer shown in FIG. 1.

Regardless of whether the polarizer 60 is used, and because the optical axis is not changed even if polarization is switched, the polarizer 60 may be installed theoretically in any part of the reflectance measuring apparatus 1. However, as a matter of fact, it may have design errors because possibly it may not have been manufactured according to its design values, and installation errors when it is installed. As shown in FIGS. 4 and 5, design and installation errors of the polarizer 60 will cause an angular shift in which the optical axial angle of an outgoing light shifts from the ideal optical axis, and a positional shift in which the position of the optical axis of the outgoing light shifts from the ideal optical axis, and thus, depending on the place where the polarizer 60 is installed, an effect produced on the performance of the reflectance measuring apparatus 1 differs. Here, FIG. 4 is a view showing an angular shift of the optical axis of an outgoing light by the polarizer 60, and FIG. 5 is a view showing a positional shift of the optical axis of the outgoing light by the polarizer 60.

Figure 6:
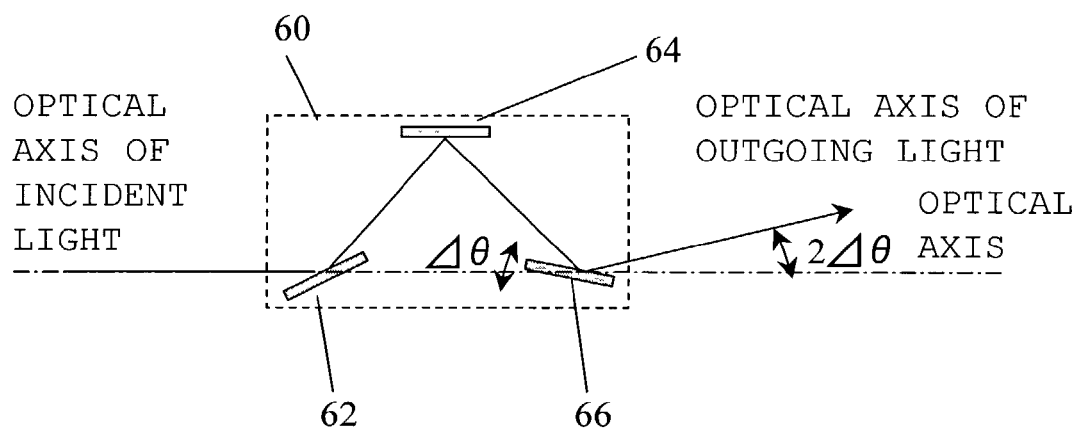
FIG. 6 is a view showing an angular shift of the optical axis of the outgoing light due to a design error of the polarizer shown in FIG. 1.
Figure 7:
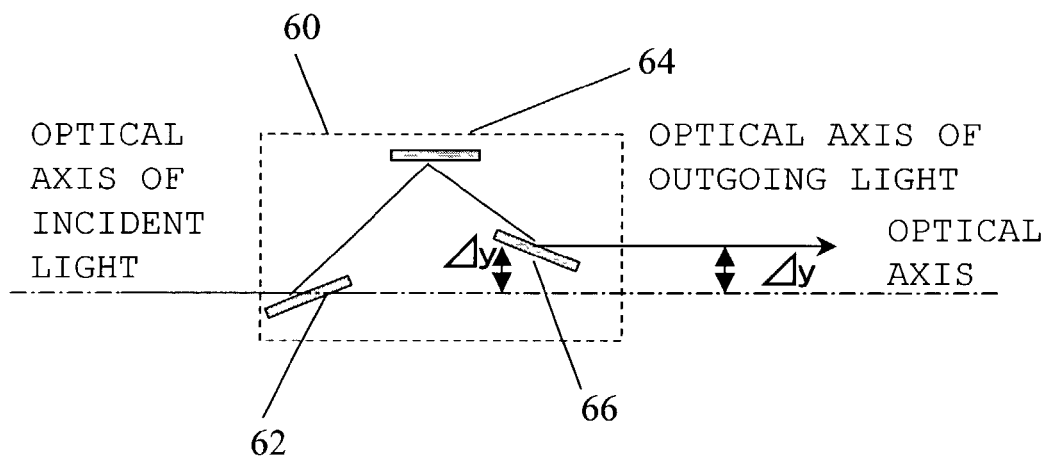
FIG. 7 is a view showing a positional shift of the optical axis of the outgoing light due to the design error of the polarizer shown in FIG. 1.

Referring to FIGS. 6~9, a detailed description will be given here of an angular and a positional shift of the polarizer 60 by taking the arrangement of the first to third multilayer mirrors 62~66 of FIG. 2 as an example. FIG. 6 is a view showing an angular shift due to a design error of the polarizer 60, FIG. 7 a view showing a positional shift due to the design error of the polarizer 60, FIG. 8 a view showing an angular shift due to an installation error of the polarizer 60, and FIG. 9 a view showing a positional error due to the installation error of the polarizer 60.

In reference to FIG. 6, the first and second multilayer mirrors 62 and 64 are correctly installed relative to the optical axis, but the angle of the third multilayer mirror 66 shifts by Δθ from its correct angle. In this case, the optical axial angle of the outgoing light shifts by approximately 2Δθ relative to the optical axis of the incident light. In reference to FIG. 7, the first and second multilayer mirrors 62 and 64 are correctly installed relative to the optical axis of the incident light, but the position of the third multilayer mirror 66 shifts by Δy from its original correct place. In this case, the optical axial angle of the outgoing light is parallel with the optical axis of the incident light, but the position shifts by Δy.

Figure 8:
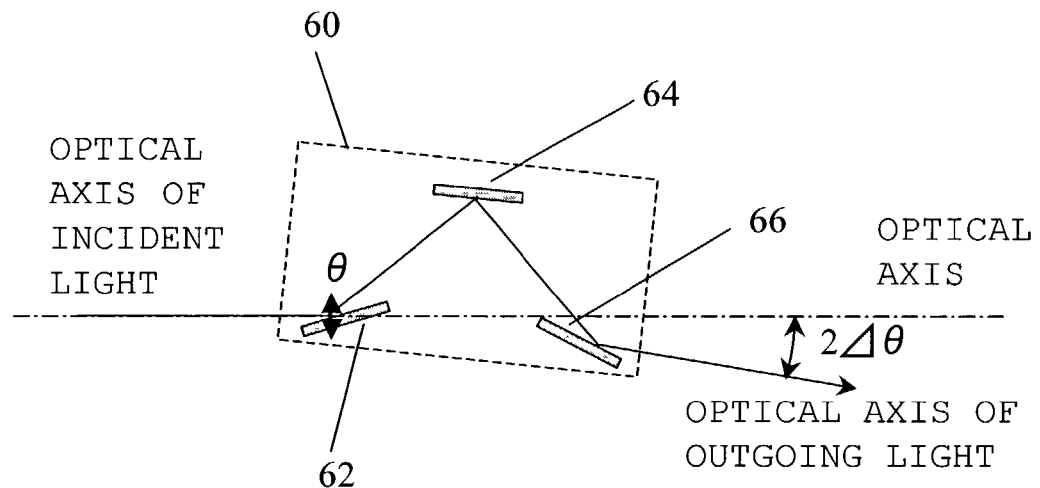
FIG. 8 is a view showing an angular shift of the optical axis of the outgoing light due to an installation error of the polarizer shown in FIG. 1.
Figure 9:
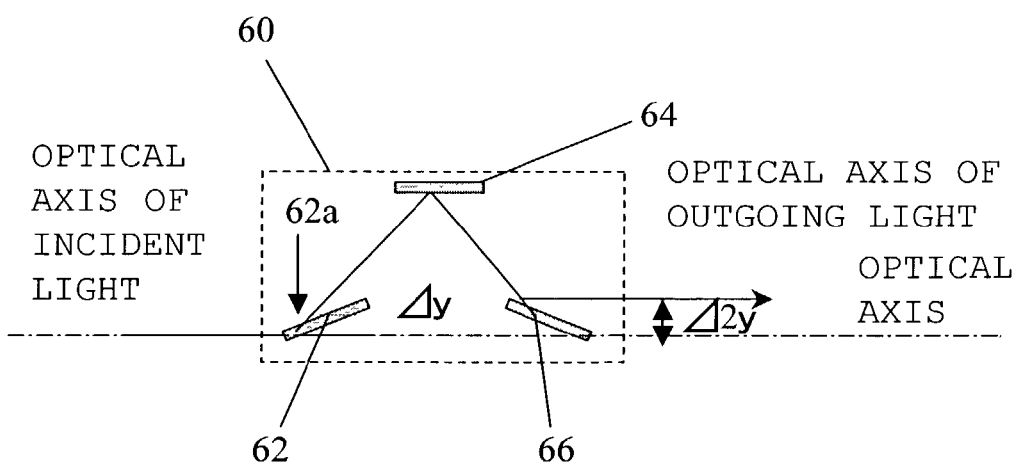
FIG. 9 is a view showing a positional shift of the optical axis of the outgoing light due to the installation error of the polarizer shown in FIG. 1.

Moreover, even though the first to third multilayer mirrors 62~66 are correctly arranged in terms of the positions, and it is an accurate polarizer in itself, it still produces errors if it is not correctly installed relative to the optical axis of an incident light. Referring to FIG. 8, the optical axial angle of the incident light entering the first multilayer mirror 62 shifts by Δθ. In this case, the optical axial angle of the outgoing light will shifts by about 2Δθ from the ideal axis. Referring to FIG. 9, the center 62a of the first multilayer mirror 62 shifts by Δy from the optical axis of the incident light. In this case, the optical axial angle of the outgoing light is parallel with the optical axis of the incident light, but the position shifts by 2Δy.

Figure 10:
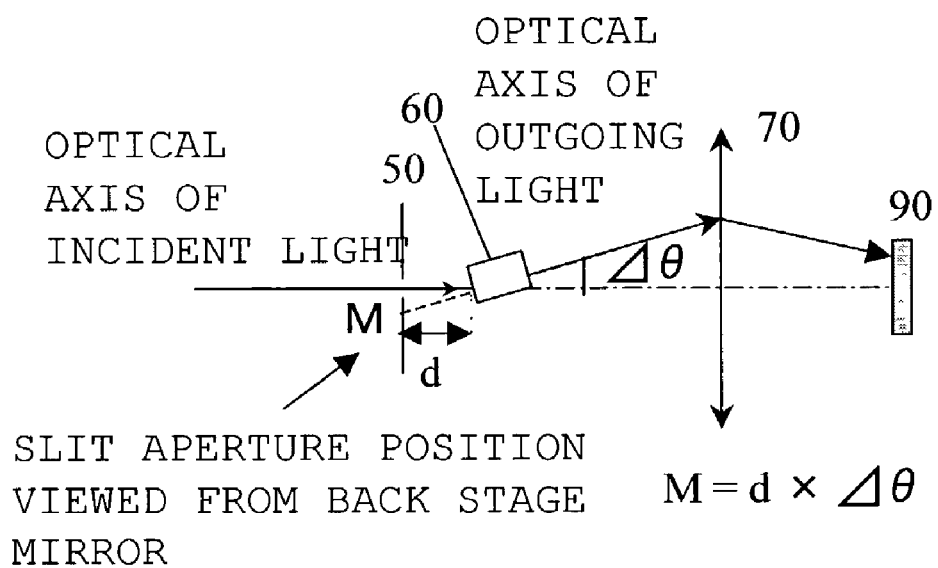
FIG. 10 is a view showing a shift of the imaging position due to the angular shift of the polarizer shown in FIG. 1.

Therefore, if an angular shift and/or positional shift is produced, it arises the problem that the image will move the ideal imaging position and that, if not image, irradiated position will move from the ideal irradiated position. FIG. 10 is a view showing a shift of the imaging position due to an angular shift of the polarizer 60. Referring to FIG. 10, the product of the optical axial angular shift Δθ of a light exiting from the polarizer 60 and the distance d from the slit 50 to the polarizer 60 is equivalent to a movement amount M of the slit 50's aperture position (i.e., an object point position) viewed from the postfocusing mirror 70. For example, assuming an error of 1 mrad is produced in the outgoing light because of the polarizer 60's installation error, if the polarizer 60 is located at a place 1 m away from the slit 50, that is equivalent to the slit 50's position having moved 1 mm, and if it is located at a place 0.1 m away, that is equivalent to the slit 50's position having moved 0.1 mm. Further, an amount of the light's movement on the measured object 90 (i.e., the movement amount of an imaging position) is equivalent to the product of the movement amount M of the aperture position of the slit 50 and the magnification of the postfocusing mirror 70. Accordingly, when there is an imaging optical system such as the postfocusing mirror 70 after the polarizer 60, installation of the polarizer 60 at a place closer to the slit 50 (namely, in a position conjugate with a measured sample) will reduce installation errors pertaining to angles of the polarizer 60.

Figure 11:
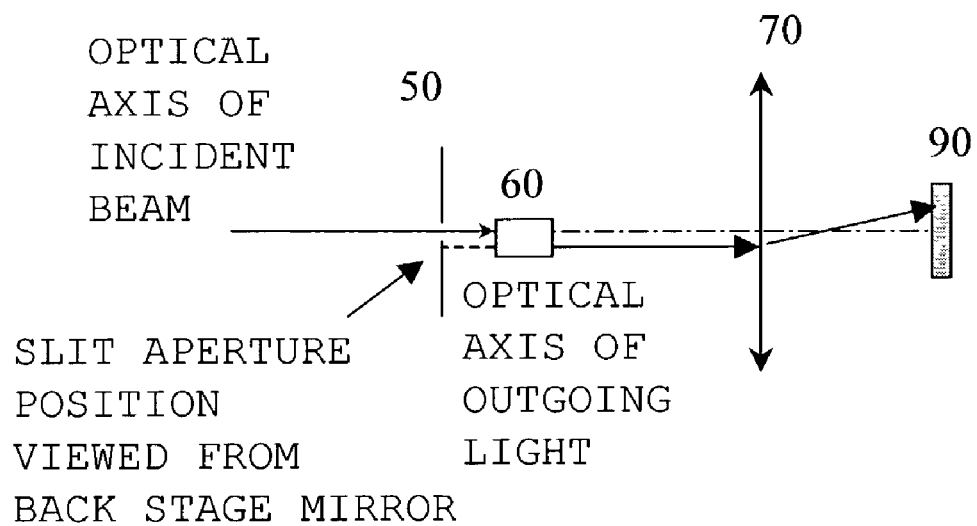
FIG. 11 is a view showing a shift in the imaging position due to the positional shift of the polarizer shown in FIG. 1.

In the meantime, the positional shift of the polarizer 60 in a direction vertical to the optical axis moves the optical axis of the outgoing light parallel, as shown in FIG. 11. Here, FIG. 11 is a view showing a shift of an imaging position due to the positional shift of the polarizer 60. By reference to FIG. 11, because of the positional shift of the polarizer 60 in the direction vertical to the optical axis, the position of the outgoing light incident on the postfocusing mirror 70 changes. However, a change of the position incident on the postfocusing mirror 70 is a parallel movement, and thus, wherever the polarizer 60 may be located ranging from the slit 50 to the back-set 70, its influence upon the incident position of the postfocusing mirror 70 is the same.

Therefore, when there is an imaging optical system such as the postfocusing mirror 70 after the polarizer 60, it is desirable to install the polarizer 60 at the slit 50 (i.e., the object point position) or as close to it as possible (at a position conjugate with it) for a positional shift of the polarizer 60. When there is no imaging optical system such as the postfocusing mirror 70 between the polarizer 60 and a measured object, an influence of an installation error can be made minimum by installing the polarizer 60 as close to the measured object 90 as possible.

Again back to FIG. 1, the postfocusing mirror 70 has a condensing function, thus forming an image of the slit 50 onto the measured object 90. The measured object 90 and the detector 80 are installed on a θ-2θ stage (not shown), thus detecting the intensity of the measured object 90's reflected light and measuring its reflectance by the detector 80.

In measuring the reflectance, non-polarized EUV light emitted from the light source 10 is imaged by the prefocusing mirror 20, and its size is reshaped by the slit 30. The EUV light with its size reshaped is diffracted into different angles per wavelength by the diffraction grating 40, being split by the slit 50. The monochromatic EUV light which comes from the slit 50 is converted into linearly polarized light by the polarizer 60, and condensed by the postfocusing mirror 70 to irradiate the measured object 90 and measure the reflectance using the detector 80. The prefocusing mirror 20, diffraction grating 40 and postfocusing mirror 70 are usually used in grazing incidence since they utilize total reflection in the X-ray region. Installation of the polarizer 60 enables selection among p-polarized light, s-polarized light, and non-polarized light, thus permitting three kinds of measurements to be performed with ease. When linearly polarized X-ray is used for measurement, a sufficient degree of polarization can be obtained.

As mentioned above, measurement of reflectance in consideration of polarization can be performed easily by combining the non-polarized light source 10, and the movable and rotational polarizer 60 with no change of the optical axis. An influence of a possible design error and installation error of the polarizer 60 can be reduced by optimizing the installation location of the polarizer 60 at the same time. Thus, the reflectance measuring apparatus 1 can measure reflectance of an optical element and the like with high precision without being influenced by a waver of polarized light.

Figure 12:
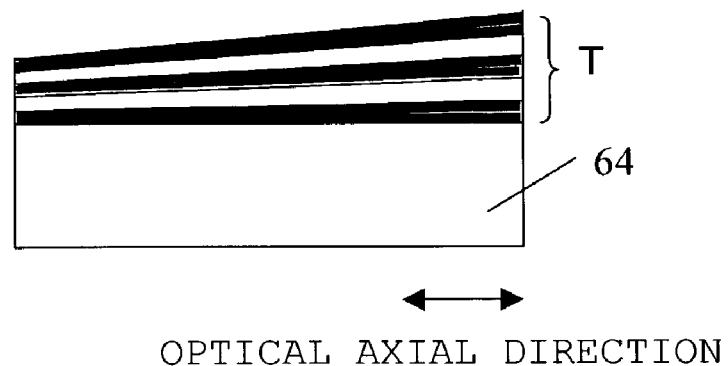
FIG. 12 is a schematic sectional view of a multilayer mirror to which a thickness distribution is applied.

Further, when a wavelength dependency is measured, the diffraction grating 40 is rotated while the slit 30 is fixed, and then, wavelength scanning is performed. Since the polarizer 60 includes the first to third multilayer mirrors 62~66, an optimal layer thickness changes according to a wavelength as approximately expressed in Bragg's equation shown in the following equation 2:

$$2d \times \cos\theta = \lambda \qquad (2)$$

where d is a thickness of layer pair, θ is an incident angle, and λ is a wavelength. So, as shown in FIG. 12, the thickness distribution T is attached to the multilayer film of the second multilayer mirror 64 as a position function. Thus, by moving only the second multilayer mirror in the optical axial direction according to the wavelength, it is possible to prevent reflectance from being lowered. Here, FIG. 12 is a schematic sectional view of the second multilayer mirror 64 to which the thickness distribution T is applied.

Figure 13:
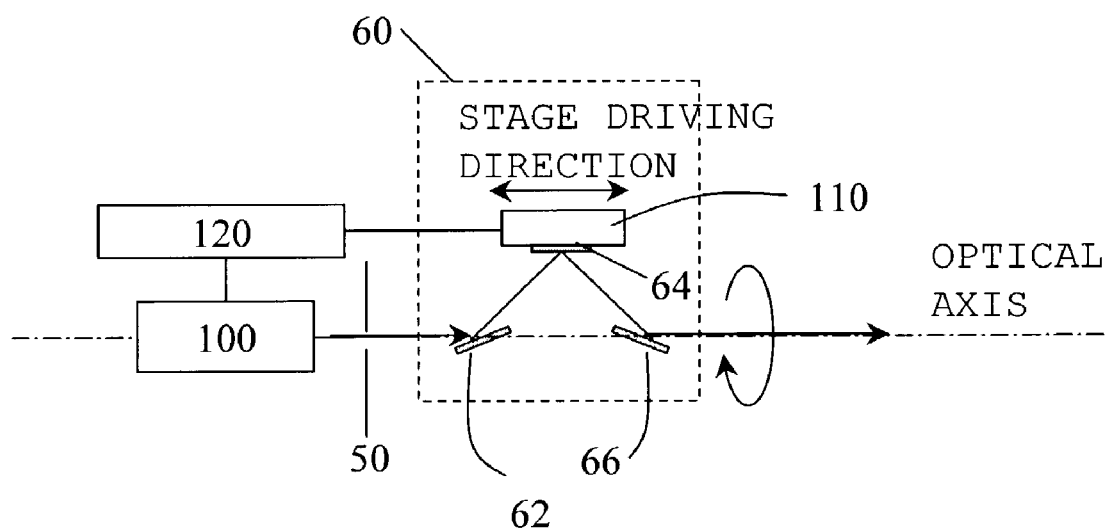
FIG. 13 is a schematic view of a layer thickness selecting apparatus.

FIG. 13 is a schematic view of a layer thickness selecting apparatus. A monochrometer 100 and a multilayer mirror drive stage 110 are connected via a controller 120, and the multilayer mirror drive stage 110 drives according to the wavelength, thus moving the second multilayer mirror 64 to an optimum thickness distribution position. Taking advantage of a difference in the angle of diffraction based on the wavelength, the monochrometer 100 arranges for only a desired wavelength to pass through the slit 50. If the polarizer 60 is located before the slit 50 and an angular shift and a positional shift of the polarizer 60 are produced, the desired wavelength cannot pass through the slit 50, and instead, a wavelength other than the desired one passes through the slit 50, thus being unable to take out light with the desired wavelength. Accordingly, it is desirable to install the polarizer 60 at a place after the slit 50. Furthermore, when the postfocusing mirror 70 is installed, it is desirable to install it as close to the slit 50 as possible, and when no postfocusing mirror 70 is installed, it is desirable to install it at a place as close to the measured object 90 as possible. In the present embodiment, although the thickness distribution T has been applied to the second multilayer mirror 64, it may be applied to the first and third multilayer mirrors 62 and 66 so that they may be moved according to a change of the wavelength.

Figure 14:
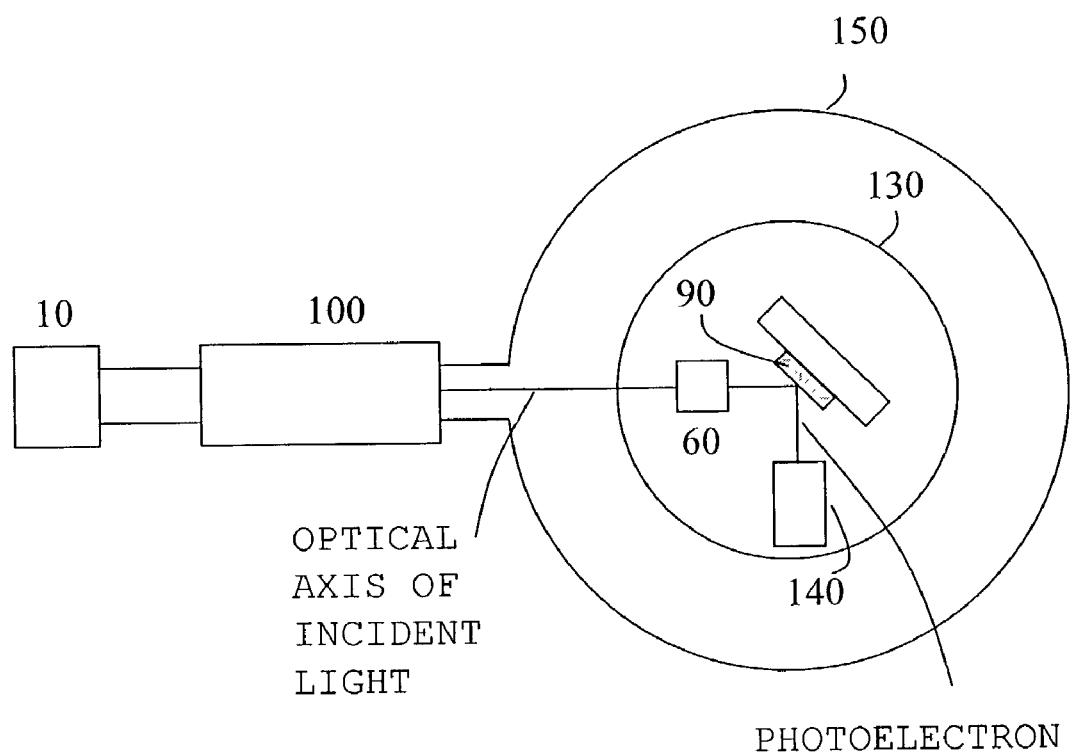
FIG. 14 is a schematic view of a photoelectron spectrometer as an example of the optical apparatus of the present invention.

Referring to FIG. 14, a description will be made below of a photoelectron spectrometer 2. FIG. 14 is a schematic view of the photoelectron spectrometer 2 of the present invention. The same reference numerals are assigned to the same members used in FIGS. 1 and 13, thus omitting repetitive explanations. The photoelectron spectrometer 2 is one of measuring apparatuses requiring linearly polarized light, which is particularly needed to measure crystals and orientation samples.

As shown in FIG. 14, the photoelectron spectrometer 2 includes a light source 10, a monochrometer 100, a polarizer 60, a rotary stage 130, an energy analyzer 140, and a vacuum chamber 150. The photoelectron spectrometer 2 irradiates high-energy, linearly polarized monochromatic light to a measured object 90 placed in the vacuum, and measures the photoelectron spectrum emitted by the external photoelectric effect. The photoelectron spectrometer 2 is an apparatus having no optical system between the monochrometer 100 and the measured object 90. For such an apparatus, fluctuations of the light position in the measured object 90 caused by setting the polarizer 60 are reduced by installing it as close to the measured object 90 as possible.

Light from the light source 10 is changed to monochromatic light by the monochrometer 100, which is, then, turned into linearly polarized light by the polarizer 60 installed close to the measured object 90, thus being irradiated to the measured object 90. The photoelectron coming out of the measured object 90 is measured and analyzed by the energy analyzer 140, thus being able to obtain information peculiar to the measured object 90. In order to obtain more detailed information, polarization planes of the polarizer 60 are switched to perform measurement again.

When a synchrotron light source is used for the light source 10, and measurement is performed without using the polarizer 60, the vacuum chamber 150 containing the measured object 90 needs to be rotated to switch the planes of polarization relative to the measured object 90. However, the structure shown in FIG. 14 makes it possible to switch the planes of polarization relative to the measured object 90 just by rotating the polarizer 60, thus enabling detail information on the measured object 90 to be obtained with ease. Therefore, the photoelectron spectrometer 2 can highly accurately measure crystals and the like used for optical elements, etc. without being influenced by a waver of polarized light.

So far, a description has been given of the reflectance measuring apparatus 1 and the photoelectron spectrometer 2 by way of example, but the present invention is not limited to these. It is effective in measuring reflection type XAFS, fluorescent XAFS, X-ray small angle scattering, soft-X-ray spectrometer, X-ray diffraction, XPS, AES, PHEED, REED, and the like all requiring polarized light.

Figure 15:
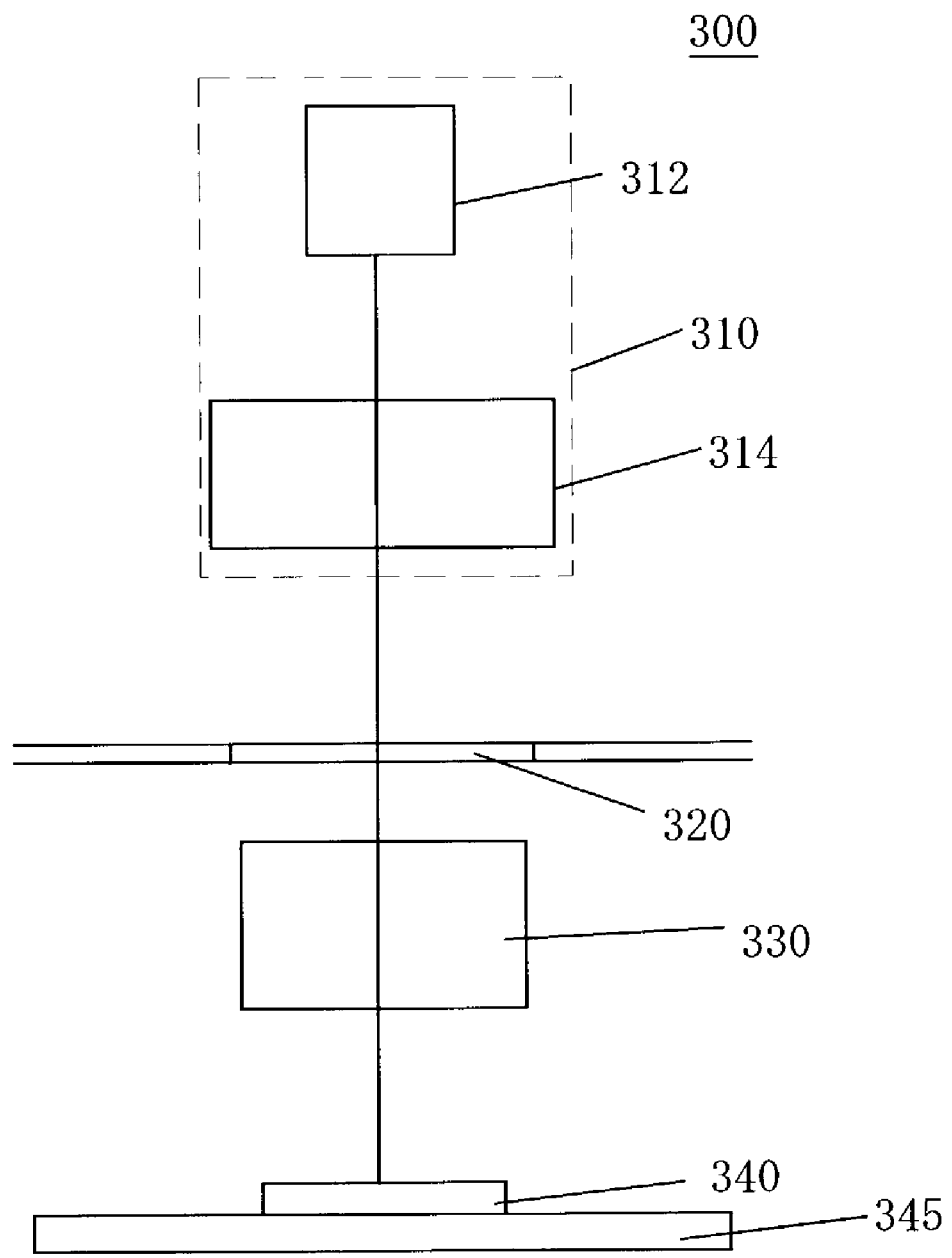
FIG. 15 is a schematic block diagram of an exemplified exposure apparatus of the present invention.

A description will be given below of an exemplified exposure apparatus 300 of the present invention referring to FIG. 15. Here, FIG. 15 is a schematic block diagram of the exposure apparatus 300. As shown in FIG. 15, the exposure apparatus 300 includes an illumination apparatus 310 that illuminates a mask or a reticle (these terms are used interchangeably in this application) onto which a circuit pattern is formed, a stage 345 that supports a plate, and a projection optical system 330 that projects onto the plate 340 diffracted light emitted from the illuminated mask pattern.

The exposure apparatus 300 is a projection exposure apparatus that exposes onto the plate 340 a circuit pattern created on the mask 320, e.g., in a step-and-repeat or a step-and-scan manner. Such an exposure apparatus is suitably applicable to a submicron or quarter-micron lithography process, and a description will be given below of this embodiment taking a step-and-scan exposure apparatus (which is also called "a scanner") as an example. The step-and-scan manner, as used herein, is an exposure method that exposes a mask pattern onto a wafer by continuously scanning the wafer relative to the mask, and by moving, after a shot of exposure, the wafer stepwise to the next exposure area to be shot. The step-and-repeat manner is another mode of exposure method that moves a wafer stepwise to an exposure area for the next shot every shot of cell projection onto the wafer.

The illumination apparatus 310, which illuminates the mask 320 onto which a circuit pattern to be transferred is created, includes a light source section 312 and an illumination optical system 314.

The light source section 312 uses, e.g., a synchrotron light source or LPP light source as a light source.

The illumination optical system 314 is an optical system that illuminates the mask 320, and includes a mirror, a light integrator, a stop, etc. For such an optical element as a mirror for the illumination optical system 314, an optical system can be used that has been determined to have optical characteristic with specified values by the optical apparatus of the present invention.

The mask 320 is, on which a circuit pattern (or an image) to be transferred is created, supported and driven by a mask stage (not shown). Diffracted light emitted from the mask 320 passes the projection optical system 330, thus and then is projected onto the plate 340. The plate 340 is an object to be exposed such as a wafer, liquid crystal plate, and the like, onto which resist is applied. The mask 320 and the plate 340 are located in an optically conjugate relationship. When the exposure apparatus 300 is a scanner, it scans the mask 320 and the plate 340 to transfer a pattern on the mask 320 onto the plate 340. When it is a stepper, the mask 320 and the plate 340 are kept stationary for exposure.

The projection optical system 330 may use a full mirror type optical system, and so on. For such an optical element as a mirror for the projection optical system 330, an optical system can be used that has been determined to have optical characteristics with specified values by the optical apparatus of the present invention.

Photo-resist is applied onto the plate 340. A photo-resist application step includes a pretreatment, an adhesion accelerator application treatment, a photo-resist application treatment, and a pre-bake treatment. The pretreatment includes cleaning, drying, etc. The adhesion accelerator application treatment is a surface reforming process so as to enhance the adhesion between the photo-resist and a base (i.e., a process to increase the hydrophobicity by applying a surface active agent), through a coat or vaporous process using an organic film such as HMDS (Hexamethyl-disilazane). The pre-bake treatment is a baking (or burning) step, softer than that after development, which removes the solvent.

The stage 345 supports the plate 340. The stage 345 may use any structure known in the art, and thus, a detailed description of its structure and operations is omitted here. For example, the stage 345 uses a linear motor to move the plate 340 in X-Y directions. The mask 320 and plate 340 are, for example, scanned synchronously, and the positions of the stage 345 and a mask stage (not shown) are monitored, for example, by a laser interferometer and the like, so that both are driven at a constant speed ratio. The stage 345 is installed on a stage surface plate supported on the floor and the like, for example, via a damper, and the mask stage and the projection optical system 330 are installed on a body tube surface plate (not shown) supported, for example, via a damper to the base-frame placed on the floor.

In exposure operation, light emitted from the light source section 312, e.g., Koehler-illuminates the mask 320 via the illumination optical system 314. Light that passes through the mask 320 and reflects the mask pattern is imaged onto the plate 340 by the projection optical system 330. The illumination optical system 314 and the projection optical system 330, which the exposure apparatus 300 uses, include optical elements whose optical characteristics are determined to meet specified values by the optical apparatus of this invention, and transmit ultraviolet light, far ultraviolet light, and vacuum violet light with high transmittance, thus providing devices (such as semiconductor devices, LCD devices, photographing devices (such as CCDs, etc.), thin film magnetic heads, and the like) with high throughput and economical efficiency.

Figure 16:
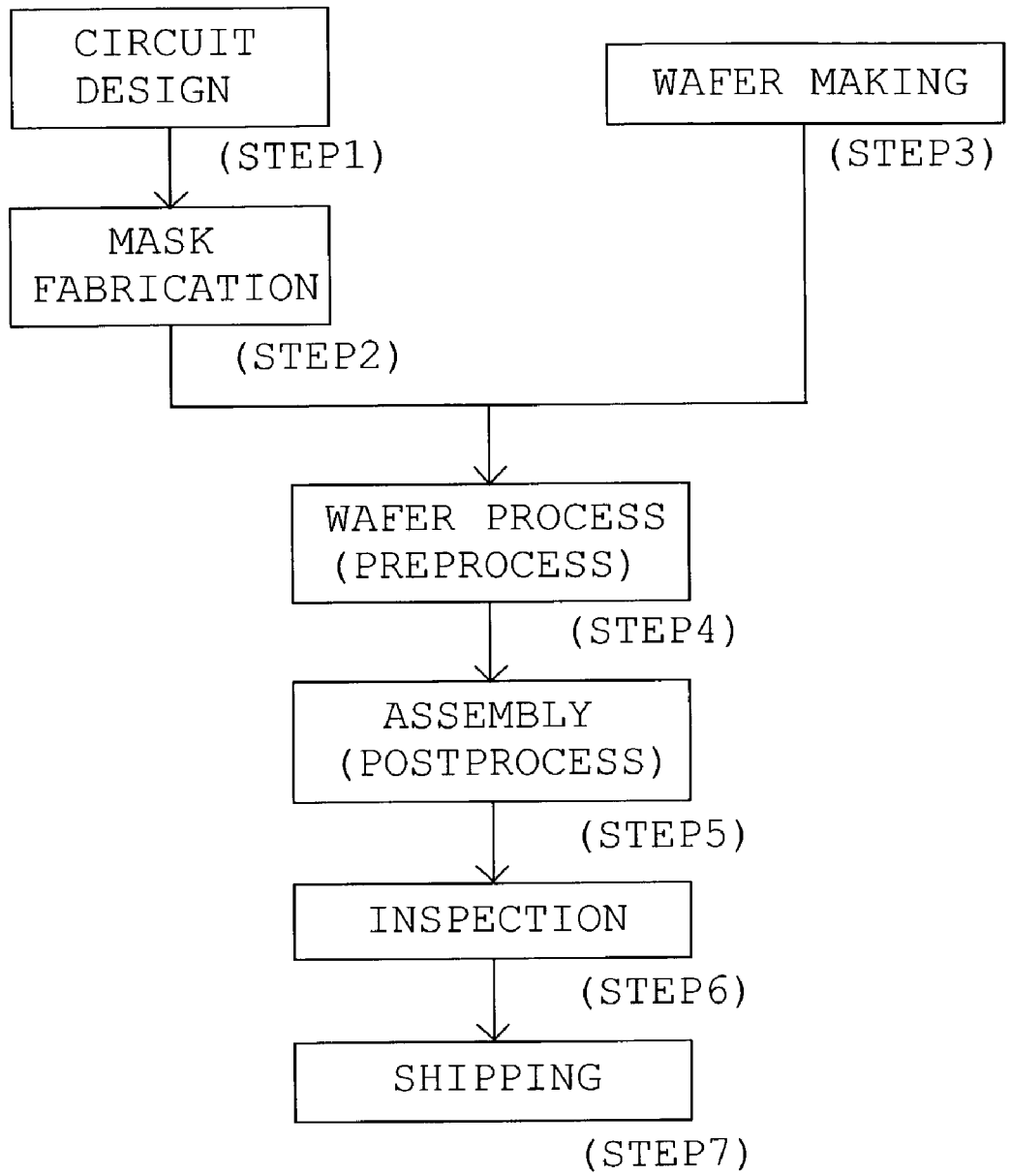
FIG. 16 is a flowchart for explaining a device fabricating method using the exposure apparatus of the present invention.
Figure 17:
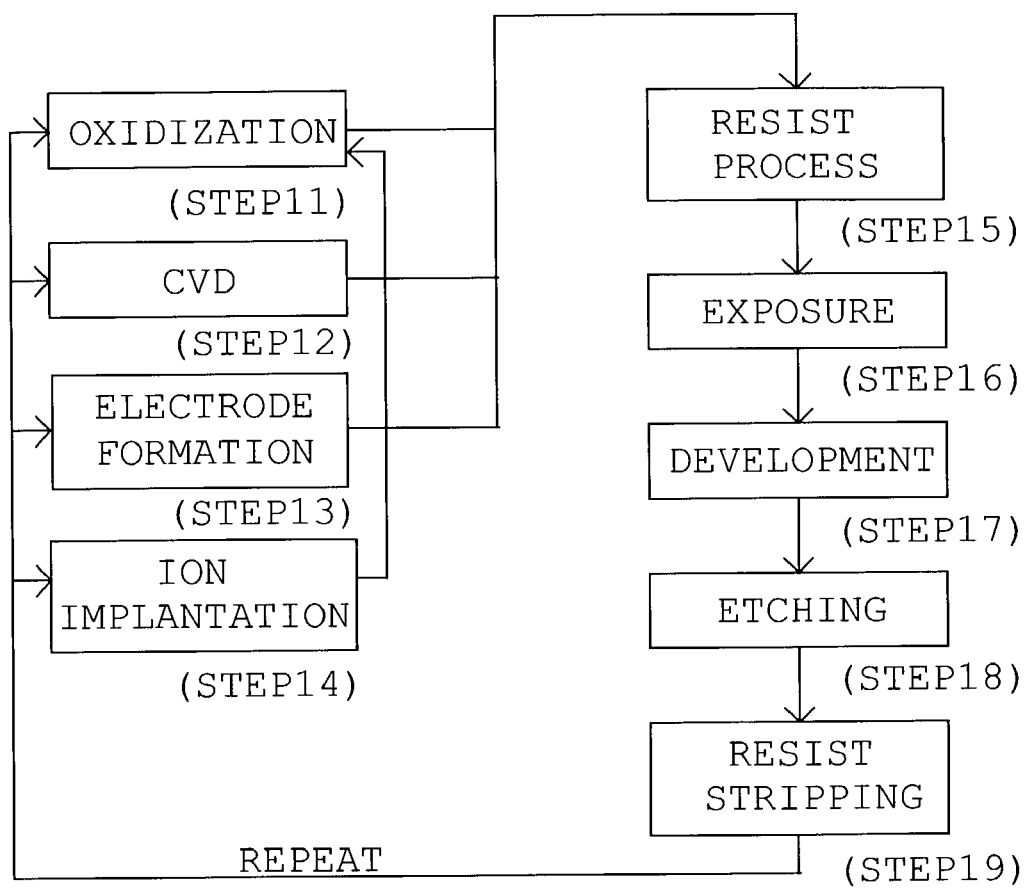
FIG. 17 is a detail flowchart for Step 4 shown in FIG. 16.
Figure 18:
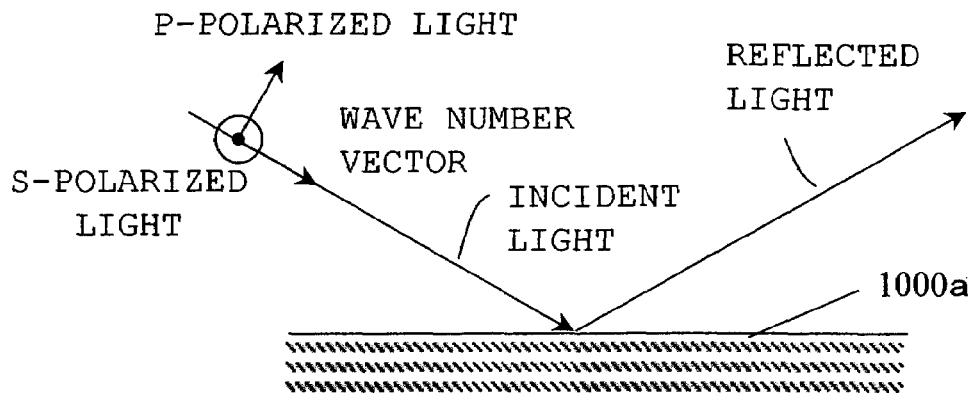
FIG. 18 is a schematic view of the polarization status of the light.
Figure 19:
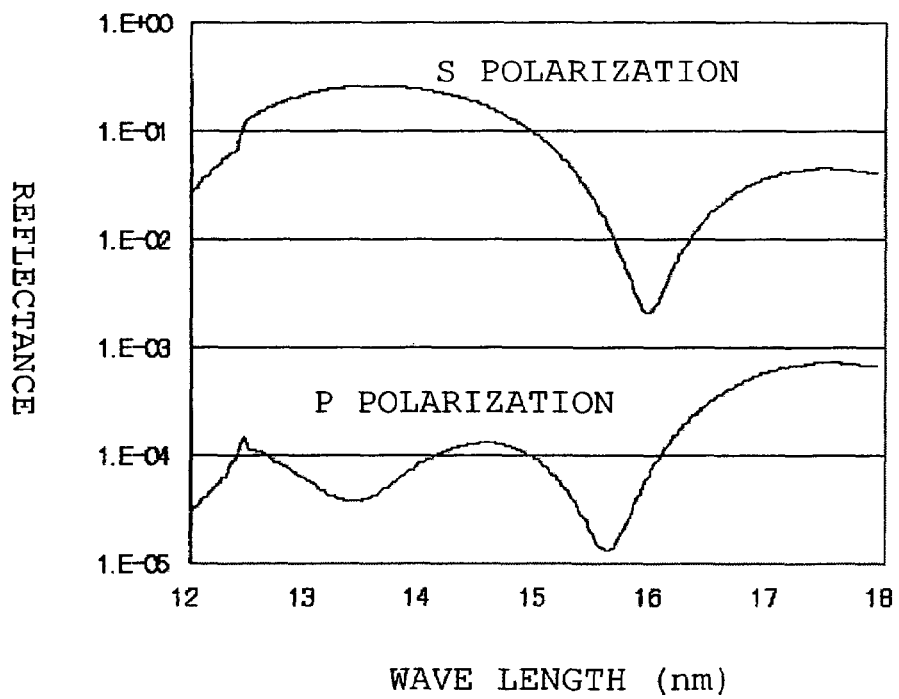
FIG. 19 is a graph showing reflectance characteristics of a multilayer mirror.
Figure 20:
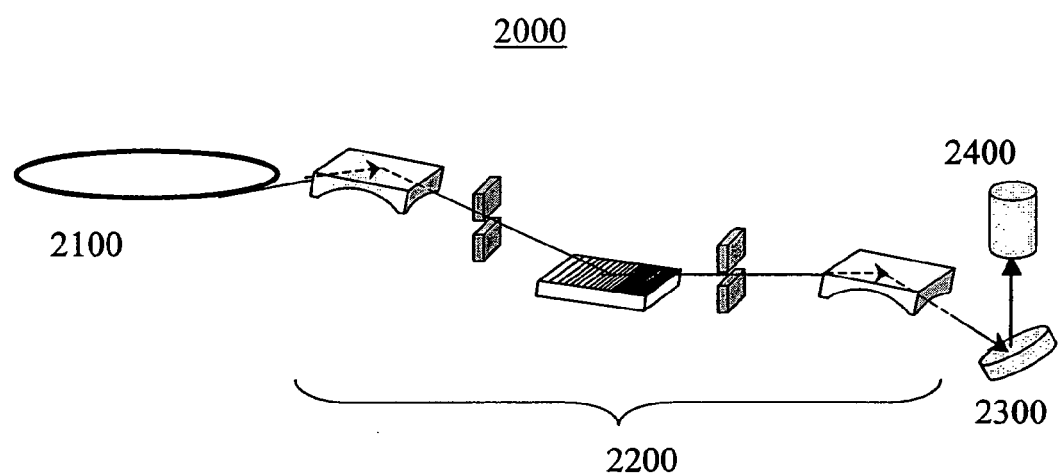
FIG. 20 is a schematic view of a reflectometer using a synchrotron light source.

Referring to FIGS. 16 and 17, a description will now be given of an embodiment of a device fabricating method using the above mentioned exposure apparatus 1. FIG. 16 is a flowchart for explaining how to fabricate devices (i.e., semiconductor chips such as IC and LSI, LCDs, CCDs). Here, a description will be given of the fabrication of a semiconductor chip as an example. Step 1 (circuit design) designs a semiconductor device circuit. Step 2 (mask fabrication) forms a mask having a designed circuit pattern. Step 3 (wafer making) manufactures a wafer using materials such as silicon. Step 4 (wafer process), which is also referred to as a pretreatment, forms actual circuitry on the wafer through lithography using the mask and wafer. Step 5 (assembly), which is also referred to as a post-treatment, forms into a semiconductor chip the wafer formed in step 4 and includes an assembly step (e.g., dicing, bonding), a packaging step (chip sealing), and the like. Step 6 (inspection) performs various tests for the semiconductor device made in Step 5, such as a validity test and a durability test. Through these steps, a semiconductor device is finished and shipped (Step 7).

FIG. 17 is a detailed flowchart of the wafer process in Step 4. Step 11 (oxidation) oxidizes the wafer's surface. Step 12 (CVD) forms an insulating film on the wafer's surface. Step 13 (electrode formation) forms electrodes on the wafer by vapor disposition and the like. Step 14 (ion implantation) implants ion into the wafer. Step 15 (resist process) applies a photosensitive material onto the wafer. Step 16 (exposure) uses the exposure apparatus 300 to expose a circuit pattern on the mask onto the wafer. Step 17 (development) develops the exposed wafer. Step 18 (etching) etches parts other than a developed resist image. Step 19 (resist stripping) removes disused resist after etching. These steps are repeated, and multi-layer circuit patterns are formed on the wafer. Use of the fabricating method in this embodiment helps fabricate higher-quality devices than ever.

So far, a description has been given of the preferred embodiments of the present invention, but the present invention is not limited to these preferred embodiments, and various modifications and changes may be made in the present invention without departing from the spirit and scope thereof.

According to the present invention, use of a light source with non-linearly polarized light and a polarizer that changes it into linearly polarized light without changing the optical axis makes it possible to create linearly polarized light that has a high degree of polarization and whose planes of polarization can be switched, and to easily measure polarization dependent characteristics of highly accurate measured samples. Further, it is possible to reduce an influence of a fluctuation in an irradiation position on a measured object and a fluctuation in an angle incident on the measured object by optimizing the installation location of the polarizer, when there are design errors and installation errors of the polarizer.

What is claimed is:

1. An optical apparatus that measures a characteristic of an optical element, said optical apparatus comprising:
   a polarizer configured to emit predetermined linearly polarized light to be incident upon the optical element by reflecting, at least three times, non-polarized light incident upon said polarizer in an extreme ultraviolet region or an X-ray region;
   a driving mechanism configured to rotate said polarizer around a predetermined rotational axis, said driving mechanism enabling said polarizer to form two linearly polarized lights having two polarized directions that are orthogonal to each other; and
   a detector configured to receive light from the optical element,
   wherein the incident light that is incident upon said polarizer and outgoing light that is emitted from said polarizer travel along the rotating axis.

2. An optical apparatus according to claim 1, wherein said polarizer is retractable from a light path of the incident light.

3. An optical apparatus according to claim 1, further comprising:
   an optical system, between said polarizer and the optical element, configured to make said polarizer and the optical element be substantially conjugate.

4. An optical apparatus according to claim 1, wherein said polarizer is arranged close to the optical element.

5. An optical apparatus according to claim 1, wherein the light source is an LPP light source.

6. An optical apparatus according to claim 1, further comprising a monochrometer for introducing to the polarizer light having a desired wavelength among the light from the light source.

7. An optical apparatus according to claim 6, wherein said polarizer includes a multilayer mirror that has a multilayer coating having a predetermined thickness distribution, and moves in accordance with the wavelength of the light from the monochrometer.

8. An optical apparatus according to claim 1, wherein the characteristic of the optical element is reflectance.

9. An optical apparatus according to claim 1, wherein the characteristic of the optical element is a photoelectron spectrum of the optical element.

10. An optical apparatus according to claim 1, wherein the polarizer reflects the incident light at a Brewster angle.

11. An optical apparatus according to claim 1, wherein the optical element is a multilayer mirror.

12. An optical apparatus according to claim 1, wherein said optical apparatus has:
   a first mode for detecting light via the optical element when one of the two linearly polarized lights is incidence to the optical element; and
   a second mode for detecting light via the optical element when other of the two linearly polarized lights is incidence to the optical element.

13. An optical element whose a characteristic is measured by using an optical apparatus that measures characteristics of said optical element, the optical apparatus comprising a polarizer configured to emit predetermined linearly polarized light to be incident upon the optical element by reflecting, at least three times, non-polarized light incident upon said polarizer in an extreme ultraviolet region or an X-ray region a driving mechanism configured to rotate said polarizer around a predetermined rotational axis, said driving mechanism enabling said polarizer to form two linearly polarized lights having two polarized directions that are orthogonal to each other, and a detector configured to receive light from the optical element, wherein the incident light that is incident upon said polarizer and outgoing light that is emitted from said polarizer travel along the rotating axis.

14. An optical element according to claim 13, wherein the optical element is a mirror, diffraction grating, an optical film, a light integrator, or a combination thereof.

15. An exposure apparatus for irradiating exposure light to a target via an optical system including an optical element whose a characteristic is measured by using an optical apparatus that measures characteristics of said optical element, the optical apparatus comprising a polarizer configured to emit predetermined linearly polarized light to be incident upon the optical element by reflecting, at least three times, non-polarized light incident upon said polarizer in an extreme ultraviolet region or an X-ray region a driving mechanism configured to rotate said polarizer around a predetermined rotational axis, said driving mechanism enabling said polarizer to form two linearly polarized lights having two polarized directions that are orthogonal to each other, and a detector configured to receive light from the optical element, wherein the incident light that is incident upon said polarizer and outgoing light that is emitted from said polarizer travel along the rotating axis, the characteristic measured being more than a specified value.

16. A device fabricating method comprising the steps of:

exposing a target using an exposure apparatus that irradiates exposure light to an object to be exposed via an optical system including an optical element whose a characteristic is measured by using an optical apparatus that measures characteristics of said optical element, the optical apparatus comprising a polarizer configured to emit predetermined linearly polarized light to be incident upon the optical element by reflecting, at least three times, non-polarized light incident upon said polarizer in an extreme ultraviolet region or an X-ray region a driving mechanism configured to rotate said polarizer around a predetermined rotational axis, said driving mechanism enabling said polarizer to form two linearly polarized lights having two polarized directions that are orthogonal to each other, and a detector configured to receive light from the optical element, wherein the incident light that is incident upon said polarizer and outgoing light that is emitted from said polarizer travel along the rotating axis, the characteristic measured being more than specified values; and performing a predetermined process for the target exposed.

* * * * *